United States Patent [19]

Littleford

[11] 4,166,469
[45] Sep. 4, 1979

[54] APPARATUS AND METHOD FOR INSERTING AN ELECTRODE

[76] Inventor: Philip O. Littleford, 500 E. Rollins, Orlando, Fla. 32803

[21] Appl. No.: 860,246

[22] Filed: Dec. 13, 1977

[51] Int. Cl.² ............................................. A61N 1/18
[52] U.S. Cl. ................................. 128/784; 128/214.4; 128/347; 128/419 P
[58] Field of Search .................... 128/404, 418, 419 P, 128/2 M, 214.4, 347, 348, DIG. 9

[56] References Cited

U.S. PATENT DOCUMENTS

| | | | |
|---|---|---|---|
| 3,087,486 | 4/1963 | Kilpatrick | 128/418 X |
| 3,545,443 | 12/1970 | Ansari | 128/214.4 X |
| 3,568,660 | 3/1971 | Crites et al. | 128/419 P X |
| 3,570,485 | 3/1971 | Reilly | 128/214.4 |
| 3,611,965 | 10/1971 | Lange | 128/214.4 X |
| 3,680,544 | 8/1972 | Shinnick et al. | 128/418 X |
| 3,792,703 | 2/1974 | Moorehead | 128/214.4 |
| 3,902,501 | 9/1975 | Citron et al. | 128/418 |
| 3,952,742 | 4/1976 | Taylor | 128/418 X |

OTHER PUBLICATIONS

Friesen et al., "Percutaneous Insertion . . . Subclovian Vein", The Canadian J. of Surg., Mar. 1977, vol. 20, pp. 131-133, 135.
Jachuck et al., "Permanent Cardiac Pacing . . . Vein", Br. J. Surg., vol. 61, 1974, 373-376.

Primary Examiner—Lee S. Cohen

[57] ABSTRACT

An apparatus and method are disclosed for implanting a pacemaker within a patient with a minimal amount of incision. The pacemaker comprises an encapsulated pulse generator having a receptacle and an electrode having an electrode tip and an electrode connector plug. The electrode connector plug is receivable in the receptacle of the encapsulated pulse generator. A needle is inserted through the exterior skin of the patient to puncture the subclavian vein. An introducer sleeve which is severed or is severable along the length thereof, is inserted into the puncture in the subclavian vein. The introducer sleeve may be introduced through the needle or on the outer surface of a needle, or through the use of a guide wire passed through the internal portion of the needle after the needle is removed. The electrode tip is inserted through the introducer sleeve to enter the vein of the patient. The electrode is moved along the vein to enter the heart of the patient. The introducer sleeve is withdrawn from the patient while the electrode is moved through a severing in the sleeve wall along the entire length thereof to remove the sleeve over the connector plug of the electrode. The electrode connector plug is connected to the receptacle of the encapsulated pulse generator and the pulse generator is implanted in the patient.

13 Claims, 20 Drawing Figures

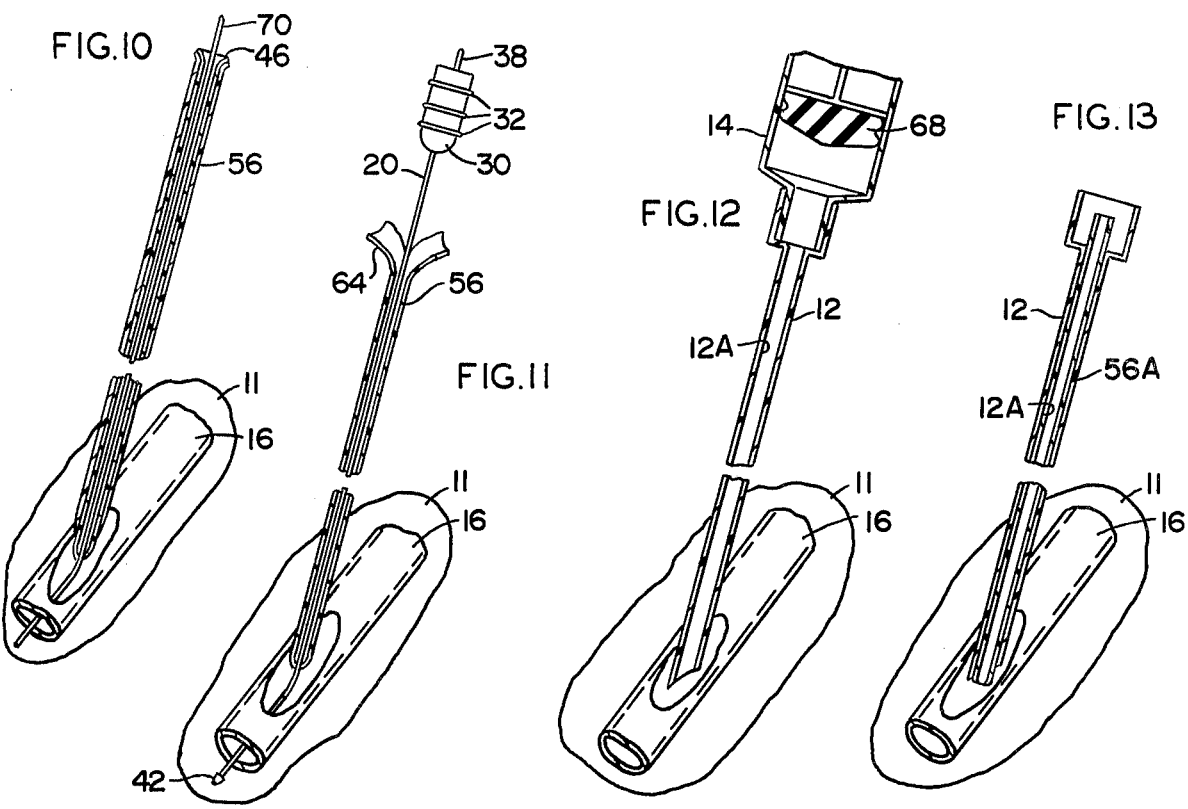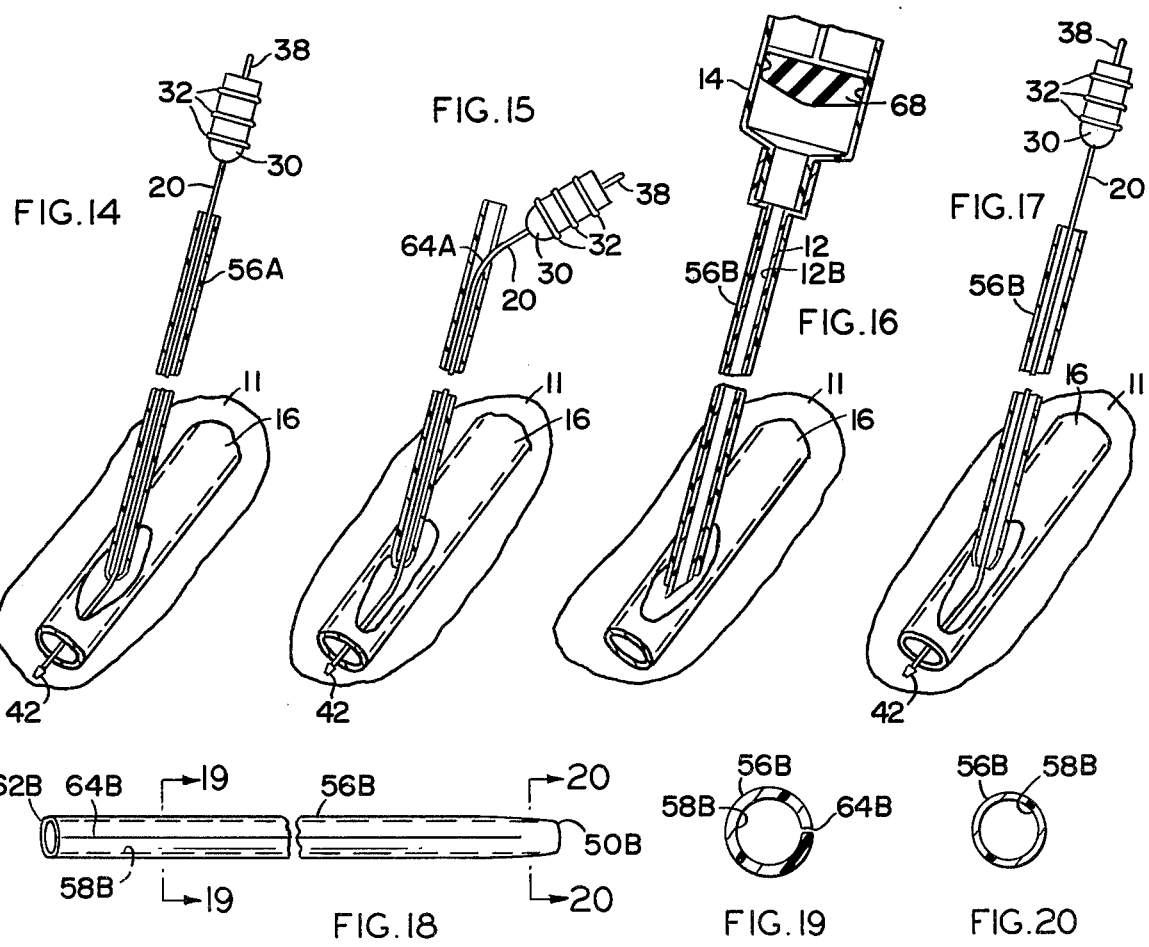

APPARATUS AND METHOD FOR INSERTING AN ELECTRODE

BACKGROUND OF THE INVENTION

1. Field of the Invention

This invention relates to surgery and more particularly to light, thermal and electrical applications comprising electrical systems. The electrical system is commonly called a pacemaker.

2. Description of the Prior Art

The field of medical technology has experienced unprecedented developments in the last several decades. Some of the most dramatic advances in the medical field have occurred in the understanding and control of the human heart. The development of the pacemaker has solved some of the heretofore unsolvable problems of heart disease and has extended the lives of thousands of patients. Presently, a surgical implant of a pacemaker and pacemaker electrode requires approximately 1-2 hours of surgical time. This surgical procedure comprises sectioning through the tissue layers of the patient down to the cephalic vein. An incision is made in the cephalic vein and the electrode tip is inserted through the incision and directed toward the heart. Further insertion of the electrode through the cephalic vein enables entry of the electrode tip into the right ventricle of the heart. The electrode is then tied to the body tissue and a second surface incision is made for receiving the pacemaker pulse generator. The electrode is connected to the pulse generator by a special plug-receptacle combination. The pacemaker is then implanted within the patient.

The cephalic vein is located beneath the layers of the pectoralis muscle on the chest wall. Many times a large physical incision and a considerable amount of dissection is required to isolate the cephalic vein. Not infrequently, the cephalic vein is too small to accommodate the size of the state-of-the-art pacemaker electrodes. In such a case, more extensive dissection must be made in following the cephalic vein to its origin. The cephalic vein extends beneath the clavicle, running ultimately to the subclavian vein. The subclavian vein is presently inaccessible by known surgical techniques to direct surgical insertion of a permanent electrode.

Others in the prior art have inserted temporary electrodes directly into a patient through the use of a surgical needle. The needle is introduced into a patient and the electrode tip is inserted through a center passage in the needle to enter an organ of the patient. The other end of the electrode is temporarily connected to an electronic device or the like.

Pacemaker electrodes generally have an electrode tip and electrode plug on opposite ends thereof. Accordingly, a permanent pacemaker electrode cannot be inserted through a needle since the needle cannot be removed over the electrode plug. The electrode cannot be electrically connected to the electrode plug by soldering or other means after the electrode is inserted since the electrode must be sterile.

The present state of the art has not provided an apparatus nor a method for quickly and efficiently inserting a permanent pacemaker electrode into the heart cavity without sectioning to a vein of a patient. The prior art has provided rapid insertion for only temporary electrodes into a patient.

Therefore it is an object of this invention to provide an apparatus and a method which overcomes the aforementioned inadequacies of the prior art devices and methods and provides an improvement which is a significant contribution to the advancement of the pacemaker art.

Another object of this invention is to provide a method and an apparatus for implanting a permanent pacemaker electrode wherein the electrode is inserted into a vein in fluid communication with the heart without sectioning the patient to gain access to the vein.

Another object of this invention is to provide a method and an apparatus for inserting a permanent electrode into an internal organ of the patient utilizing an introducer sleeve in cooperation with a needle. The needle is inserted through the exterior skin of the patient to puncture the internal organ. The introducer sleeve is inserted into the puncture in the internal organ and the needle is removed. The electrode is then inserted through the introducer sleeve enabling the introducer sleeve to be withdrawn through a severing in the sleeve wall along the length thereof.

Another object of this invention is to provide a method and an apparatus for inserting a permanent electrode into an internal organ of a patient incorporating an introducer sleeve made of a substantially rigid plastic or fiberous material which has a severing means for severing the sleeve wall along the entire length thereof. The severing in the sleeve allows the sleeve to be removed from the electrode over an electrode plug at the terminal end of the electrode.

Another object of this invention is to provide a method and an apparatus for inserting a permanent electrode into an internal organ of a patient wherein the introducer sleeve includes perforations along the length thereof for enabling the sleeve to be severed to remove the sleeve over the electrode plug at the terminal end of the electrode.

Another object of this invention is to provide a method and an apparatus for inserting a permanent electrode into an internal organ of a patient incorporating an introducer, an introducer sleeve, a guide wire and a needle.

Another object of this invention is to provide a method and an apparatus for inserting a permanent electrode into an internal organ of a patient comprising an introducer sleeve which is severed along the entire length thereof except the tip portion of the introducer sleeve.

Another object of this invention is to provide a method and an apparatus for inserting a permanent electrode into an internal organ of a patient wherein an introducer sleeve is insertable on the outer surface of a needle into the internal organ of the patient.

Another object of this invention is to provide a method and an apparatus for inserting a permanent electrode into an internal organ of a patient wherein an introducer and an introducer sleeve is inserted by a guide wire into the internal organ of the patient.

SUMMARY OF THE INVENTION

The invention may be incorporated into the method of inserting a permanent electrode into an internal organ of a patient wherein the electrode has an electrode tip at one end and a connector plug at the other end. The method is suitable for implanting a pacemaker within a patient wherein the pacemaker comprises an encapsulated pulse generator having a receptacle for receiving the connector plug of the electrode. The method includes inserting a needle through the skin of the patient to puncture the internal organ of the patient. An introducer sleeve is introduced within the patient to communicate with the puncture in the internal organ of the patient. The electrode tip is introduced through the introducer sleeve to enter the organ of the patient. The introducer sleeve is then removed from the patient through a severing in the sleeve wall of the introducer sleeve along the length thereof.

The introducer sleeve may be introduced in one of three ways. First, the introducer sleeve may be inserted through the needle puncturing the internal organ leaving the introducer sleeve communicating with the internal organ upon removing the needle. Second, the introducer sleeve may be inserted by introducing a guide wire through the needle to enter the internal organ. The needle is then withdrawn and an introducer and the introducer sleeve are inserted over the guide wire to communicate with the puncture in the internal organ. The introducer and guide wire are then removed leaving the introducer sleeve in communication with the internal organ. Third, the introducer sleeve is located on the outer surface of the needle and is inserted into the patient upon inserting the needle into the patient. The needle is then withdrawn leaving the introducer sleeve in communication with the internal organ of the patient.

When the method is applied to implanting a pacemaker, the needle is inserted through the exterior skin of the patient to puncture the subclavian vein of the patient leading directly to the heart. The introducer sleeve is then inserted within the patient to communicate with the puncture in the subclavian vein in one of the aforementioned methods. The electrode tip is guided through the introducer sleeve to enter the subclavian vein of the patient. The electrode is moved along the subclavian vein of the patient to enter the heart of the patient. The introducer sleeve is then withdrawn from the patient and the electrode is removed from the introducer sleeve through a severing in the sleeve wall along the entire length of the sleeve. The connector plug of the electrode is connected to the receptacle of the encapsulated pulse generator and the pulse generator is implanted into the patient by conventional surgical treatment.

An important aspect of the invention resides in the apparatus comprising the interrelation of the needle and the introducer sleeve. In general, the introducer sleeve comprises a plastic or fibrous material having a severing in the sleeve wall or a weakening to aid severing along at least the substantial length of the sleeve. The severing means may take the form of perforations along the entire or a substantial length of the introducer sleeve. In the alternative, the severing means may comprise a complete severing along all but the tip portion of the introducer sleeve. The severing enables the sleeve to be peeled off of the permanent electrode for removing the sleeve over the connector plug at the end of the electrode.

In the first method, a guide wire is introduced through the internal passage of the needle to enter the internal organ. The needle is withdrawn over the guide wire. An introducer has a central aperture for receiving the guide wire with the introducer sleeve closely fitting on the outer surface of the introducer. The introducer sleeve is placed on the outer surface of the introducer and the introducer is guided into the internal organ of the patient along the guide wire. The guide wire and the introducer are removed leaving the introducer sleeve.

In the second method of inserting the introducer sleeve, the introducer sleeve must be of a size sufficient to be received within an internal diameter of the internal passage of the needle. Accordingly, the sleeve is inserted through passage of the needle into communication with the internal organ.

In a third method, the introducer sleeve closely fits on the outer surface of the inserting needle. As the needle is inserted into the patient, the introducer sleeve is concomitantly inserted into communication with the internal organ. The needle is then be removed leaving the introducer sleeve.

This invention accordingly comprises an apparatus possessing the features, properties and the relation of elements which will be exemplified in the apparatus and method hereinafter described, and the scope of the invention will be indicated in the claims.

BRIEF DESCRIPTION OF THE DRAWINGS

For a fuller understanding of the nature and objects of the invention, reference should be had to the following detailed description taken in conjunction with the accompanying drawings in which:

FIG. 10 illustrates the third step in the first method wherein the introducer and the introducer sleeve shown in FIGS. 3 and 4 are inserted into fluid communication with the internal vein;

FIG. 11 is the fourth step of the first method wherein the electrode of FIG. 7 has been inserted through the introducer sleeve and the sleeve is being peeled off of the electrode to remove the sleeve over the plug at the end of the electrode;

FIG. 12 illustrates the first step of a second method of inserting the electrode into the patient wherein the needle is puncturing the internal vein of the patient;

FIG. 13 illustrates the second step of the second method wherein an introducer sleeve is inserted within the needle into fluid communication with the internal vein of a patient;

FIG. 14 illustrates the third step of the second method wherein the electrode is inserted through the introducer sleeve into the internal vein of the patient;

FIG. 15 shows the fourth step of the second method wherein the introducer sleeve is removed from the electrode;

FIG. 16 illustrates the first step of a third method of inserting the electrode into the patient wherein the needle and an introducer sleeve serially enter the internal organ of a patient;

FIG. 17 illustrates the second step of the third method wherein the electrode is inserted through the introducer sleeve upon removal of the needle;

FIG. 18 illustrates the introducer sleeve of FIG. 16 and 17 which is a variation of the introducer sleeve shown in FIG. 14;

FIG. 19 is a sectional view along line 19—19 in FIG. 18; and

FIG. 20 is a sectional view along line 20—20 in FIG. 18.

Similar reference characters refer to similar parts throughout the several views of the drawings.

DETAILED DESCRIPTION

Figure 1:
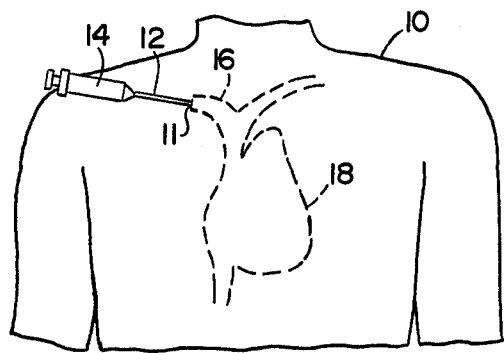
FIG. 1 is an elevational view of an apparatus and method for implanting a pacemaker into the patient showing a needle being inserted through the exterior skin to puncture the subclavian vein to communicate with the heart of the patient.

FIG. 1 is an elevational view showing the insertion of a needle 12 and a syringe 14 with the needle 12 being inserted through the exterior skin 11 of a patient 10. The needle 12 pierces the subclavian vein 16 which leads directly to the the heart 18 of patient 10. The subclavian vein is essentially inaccessible by surgical dissection. The subclavian vein is a large vein and readily receives a permanent pacemaker electrode. The insertion of the needle 12 is the first step in the method of implanting a pacemaker electrode with minimal incision to the patient. This apparatus and method will be described hereinafter.

Figure 2:
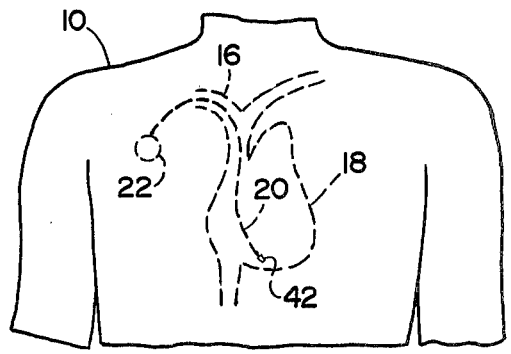
FIG. 2 illustrates the completed implant of the pulse generator and the pacemaker electrode in the patient.

FIG. 2 is an elevational view of the patient 10 with a pacemaker electrode 20 extending through the subclavian vein 16 to the heart 18. A pacemaker pulse generator 22 is shown implanted within the patient 10. The pulse generator 22 and the pacemaker electrode 20 are more fully shown in FIGS. 5–7.

The pulse generator 22 comprises an electronic circuit and power supply encapsulated in a covering 24 having an aperture 26. The pulse generator 22 includes a receptacle shown generally as a jack 28 for receiving a plug 30 of pacemaker electrode 20. The plug 30 comprises a plurality of O-rings 32 to seal with aperture 26 of covering 24. The pulse generator includes securing means for securing the plug 30 to jack 28 which is shown as a vice screw 34. The plug 30 is inserted within the receptacle jack 28 and the vice screw 34 is rotated for locking the plug 30 therein. A covering cap or plug 36 covers the end of aperture 26.

Figures 5, 6:
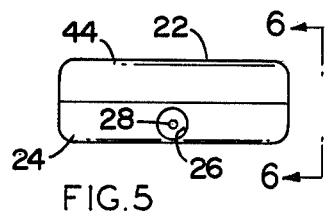
FIG. 5 is a front elevational view of a pacemaker pulse generator.
FIG. 6 is a side elevational view of the pulse generator shown in FIG. 5.
Figure 7:
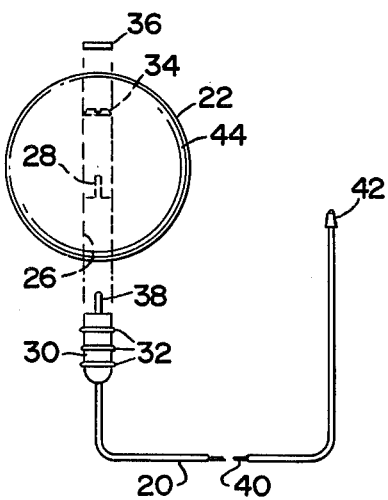
FIG. 7 is a view of the pulse generator shown in FIGS. 5 and 6 with a pacemaker electrode having an electrode tip and an electrode plug.

A connector pin 38 of plug 30 contacts the negative output of the pulse generator 22. A conductor 40 connects the connector pin 38 to an electrode tip 42 to provide a negative signal upon an output from the pulse generator 22. The positive terminal of the pulse generator 22 comprises an upper metallic electrode 44 shown in FIGS. 5–7. Although a specific example of the pacemaker pulse generator 22 and electrode 20 are used in this embodiment, it should be understood that the apparatus and method herein disclosed are not limited to such a pacemaker configuration. For example, the invention is compatible for use with an integral or one-piece pulse generator and electrode. The pulse generator 22 and the electrode 20 shown in FIGS. 5–7 are merely disclosed for clarifying the exact practice of the apparatus and method.

Figure 3:
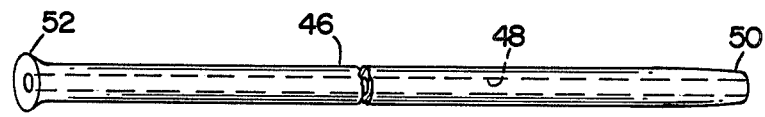
FIG. 3 is an elevational side view of an introducer used to implant the electrode in the patient.

FIG. 3 illustrates an introducer 46 which is used in a first method of inserting the pacemaker electrode 20 into the patient 10. The introducer 46 includes a through aperture 48 and a generally pointed tip portion 50. The introducer 46 also comprises a reinforced and flared base 52.

Figure 4:
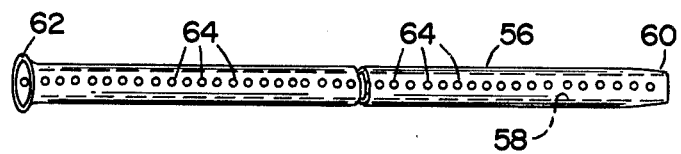
FIG. 4 is an elevational view of an introducer sleeve for use with the introducer shown in FIG. 3.

FIG. 4 illustrates an introducer sleeve 56 having a through aperture 58, a flared base 62 and a reduced sleeve wall tip 60. The introducer sleeve 56 and more particularly the aperture 58 is designed to closely fit the outer circumference of the introducer 46 with the base 62 abutting base 52 and the tip 60 tapering from the outer circumference of introducer 46. The introducer sleeve 56 also comprises severing means shown generally as 64 comprising a plurality of through apertures along the length of the introducer sleeve 56. The severing means may comprise a plurality of perforations, slots, or other weakening in one or more locations in the sleeve wall for enabling the sleeve to be severable along the length thereof. The severing means 64 may also comprise a precut in the sleeve wall along all or a substantial length of the introducer sleeve 56.

Figure 9:
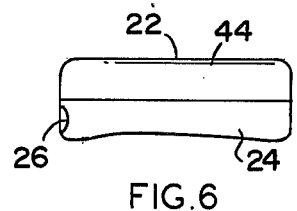
FIG. 9 illustrates the second step of the first method showing a guide wire being introduced through the needle into the internal vein.
Figure 8:
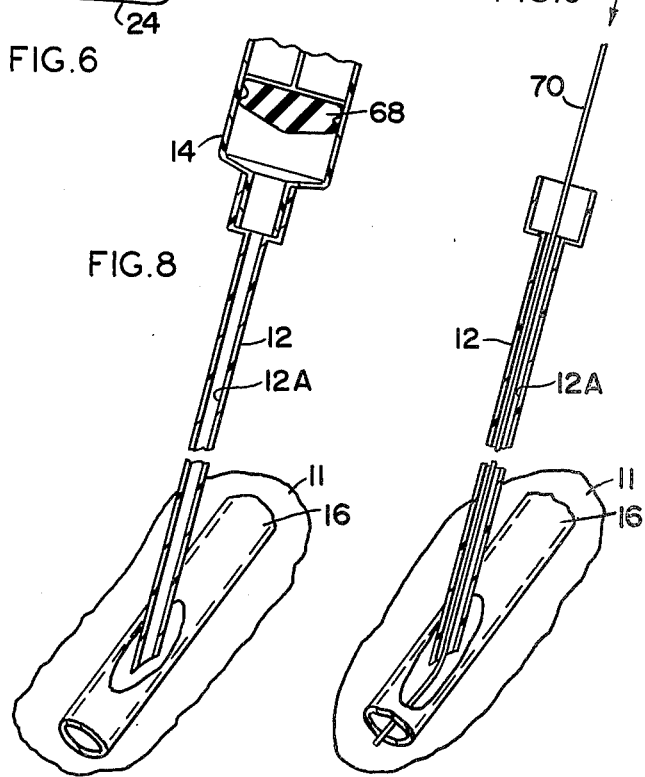
FIG. 8 illustrates the first step in a first method of introducing a permanent electrode into an internal organ of a patient wherein a needle punctures an internal vein of the patient.

FIGS. 8–11 illustrate the first through fourth steps of a first method of inserting the electrode 20 into an internal organ shown as the subclavian vein 16. FIG. 8 illustrates the needle 12 puncturing the exterior skin 11 of the patient 10 to enter the vein 16. A piston 68 of syringe 14 is withdrawn slightly to draw a small quantity of blood from vein 16 to insure that the needle 12 has entered the vein 16. The blood is returned into the vein 16 and the syringe 14 removed from needle 12 as shown in FIG. 9. A guide wire 70 has a diameter sufficiently small to enter through the internal passage 12A of needle 12. The guide wire is pushed through needle 12 to enter the vein 16 as shown in FIG. 9. The needle 12 is then removed enabling the introducer 46 and the introducer sleeve 56 to be guided along guide wire 70 to enter the vein 16 as shown in FIG. 10. The base 62 of the sleeve 56 abuts base 52 of introducer 46. The length of sleeve 56 is less than the length of introducer 46 as shown in FIGS. 3, 4 and 10. The introducer 46 adds mechanical strength to the introducer sleeve 56 during entry in the patient 10. The guide wire 70 and introducer 46 are then removed from the vein 16 leaving the introducer sleeve 56 in fluid communication with the vein 16. The pacemaker electrode tip 42 is inserted into introducer sleeve 56 to enter vein 16. The electrode 20 is pushed until the electrode tip 42 enters the heart 18 as shown in FIG. 1. The sleeve 56 is severed along the severing means 64 and concomitantly withdrawn from the patient 10 leaving the electrode tip 42 within the heart cavity. In the case of the sleeve 56 being precut, the sleeve is merely peeled off at the electrode 20. The electrode plug 30 may then be connected to the pulse generator 22. The pulse generator 22 is then implanted into the patient 10.

FIGS. 12–15 show the first four steps of a second method of introducing the electrode 20 into an internal organ of a patient. FIG. 12 illustrates the needle 12 puncturing the external skin 11 to enter the vein 16 in a manner similar to FIG. 8. The piston 68 is withdrawn drawing blood from vein 16 to insure proper entry into the vein 16. The syringe 14 is then removed enabling a sleeve 56A to be inserted within the internal passage 12A of needle 12 to enter the vein 16. The sleeve 56A is substantially tubular and having severing means 64A similar to that shown in FIG. 4. The introducer sleeve 56A does not have an expanded base 62 as in FIG. 4 which enables the needle 12 to be withdrawn over the sleeve 56A leaving the sleeve 56A within vein 16. The electrode tip 42 is inserted through the introducer sleeve 56A into the vein 16 to enter heart 18 as shown in FIG. 14. The sleeve 56A may then be removed by severing along the severing means 64A as shown in FIG. 15. The limitation of the second method shown in FIGS. 12-15 is determined by the state-of-the-art size of the electrode tip 42 shown in FIGS. 7, 14 and 15. The size of the needle used is determined by the size of the electrode tip 42. Large electrode tips require a large needle which can produce substantial tissue damage. In such a case, the first method shown in FIGS. 8-11 is preferable since the introduction of the introducer and introducer sleeve 46 and 56 as shown in FIG. 10 merely separates tissue from the original incision by needle 12 rather than cutting of the tissue. Accordingly, a smaller needle is required in the first method shown in FIGS. 8-11 than the second method shown in FIGS. 12-15.

FIGS. 16 and 17 illustrate the first and second steps of a third method of inserting a pacemaker electrode into a vein 16. In this embodiment, the introducer sleeve 56B more fully shown in FIGS. 18-20 comprises a central through aperture 58B and a tip portion 50B. FIGS. 19 and 20 illustrate sectional views of the introducer sleeve 56B showing the relative wall thicknesses at section lines 19—19 and 20—20 in FIG. 18. The severing means 64B in this embodiment comprises a cut extending from the end 62B of introducer sleeve 56 to a region within approximately five millimeters of tip 50B.

The inner aperture 58B of sleeve 56B is selected to closely receive the outer surface 12B of needle 12. The length of introducer sleeve 56B is slightly shorter than the length of needle 12 enabling the needle to make a primary puncture through the external skin 11 of the patient 10 and internal organs prior to entry by the introducer sleeve 56B. The needle 12 and sleeve 56B are inserted into communication with the vein 16 and the needle 12 is withdrawn, leaving the sleeve 56B in communication with the vein 16. The electrode 20 may then be inserted into the vein 16 and the heart 18 by the introducer sleeve 56B as shown in FIG. 17. The connector plug 30 may then be secured to the pulse generator 22 as heretofore described. In this embodiment, the needle required is larger than the method shown in FIGS. 8-11, but is generally smaller than the needle required in FIGS. 12-14. In this case, the sleeve 56B closely fits on the outer surface 12B of needle 12.

The foregoing has described three distinct methods of inserting the electrode 20 into an internal organ of the patient 10. In each case, an electrode sleeve 56 was used for introducing the electrode 20 into an internal organ of the patient 10. Mechanical strength is given to the introducer sleeve during entry into the patient 10. In the first method, the introducer aids entry of the sleeve. In the second and third methods, the needle aids entry of the sleeve. Accordingly, the introducer sleeve may be made of a lightweight material. The physical characteristics of the sleeve shown in FIGS. 4, 18-20 may be adapted to any of the three methods.

The apparatus described includes the interrelation of structural sizes of the needle, introducer sleeves and introducers. The severing means includes a structure for enabling the sleeve to be peeled off of the electrode. The severing means may take various forms such as perforations, holes, through cuts, reduced wall thickness and integral cutting agents such as strings and the like.

The method of the invention comprise the introduction of an introducer sleeve by various means. The pacemaker electrode is then inserted into the internal organ through the introducer sleeve. The sleeve is then peeled off along a severing in the length of the sleeve to remove the sleeve over the electrode plug. In the apparatus as set forth herein, the sleeve comprises severing means for enabling the severing of the sleeve along the length. In the method of this invention, external severing by a scalpel, scissors or a cutting blade is within the contemplation of the method set forth herein.

The present disclosure includes that contained in the appended claims, as well as that of the foregoing description. form with a certain degree of particularity, it is understood although this invention has been described in its preferred that the present disclosure of the preferred form has been made only by way of example and that numerous changes in the details of construction and the combination and arrangement of parts may be resorted to without departing from the spirit and the scope of the invention.

Now that the invention has been described:
What is claimed is:

1. The method of inserting an electrode into an internal organ of a patient, comprising the steps of:
   inserting a needle through the exterior skin of the patient to puncture the internal organ of the patient:
   introducing a guide wire through the needle to enter the internal organ;
   withdrawing the needle;
   introducing an introducer and an introducer sleeve over the guide wire to communicate with the puncture in the internal organ of the patient; and
   withdrawing the introducer and the guide wire;
   introducing an electrode through the introducer sleeve to enter the organ of the patient; and
   removing the introducer sleeve from the patient by peeling off the introducer sleeve from the electrode.

2. The method of inserting an electrode into an internal organ of a patient, the electrode having an electrode tip and a connector plug, comprising the steps of:
   inserting a needle through the exterior skin of the patient to puncture the internal organ;
   introducing a guide wire into the needle to enter the internal organ;
   withdrawing the needle;
   inserting an introducer and an introducer sleeve over the guide wire to communicate with the puncture in the internal organ;
   withdrawing the introducer and the guide wire;
   introducing the electrode tip of the electrode through the sleeve to enter the internal organ; and
   removing the introducer sleeve from the patient by peeling off the sleeve from the electrode along the length of the introducer sleeve to remove the sleeve over the connector plug of of the electrode.

3. The method of implanting a pacemaker within a patient, the pacemaker comprising an encapsulated pulse generator having a receptacle and an electrode having an electrode tip and an electrode connector plug cooperable with the receptacle of the encapsulated pulse generator, comprising the steps of:
   inserting a needle through the exterior skin of the patient to puncture the subclavian vein of the patient, which communicates with the heart of the patient;

inserting an introducer sleeve within the patient to communicate with the puncture in the subclavian vein of the patient;

introducing the electrode tip through the introducer sleeve to enter the subclavian vein of the patient;

moving the electrode along the subclavian vein of the patient to enter the heart of the patient;

removing the introducer sleeve from the patient by withdrawing the introducer sleeve from the patient and peeling off the introducer sleeve from the electrode along a longitudinal severing in the sleeve wall to remove the sleeve over the connector plug of the electrode;

connecting the connector plug of the electrode to the receptacle of the encapsulated pulse generator; and implanting the pulse generator into the patient.

4. An apparatus for inserting an electrode in an internal organ of a patient; the electrode having an electrode tip and a connector plug comprising in combination:

a needle for puncturing the tissue of the patient to enter the internal organ of the patient, said needle having an internal passage;

an introducer sleeve having severing means along the length thereof;

inserting means including a guide wire dimensioned to be received in said internal passage of said needle, for inserting said introducer sleeve into the puncture in the internal organ of the patient formed by said needle;

an introducer having an internal passage dimensioned to receive said guide wire therein and dimensioned to receive said introducer sleeve along the outer surface thereof;

said introducer sleeve enabling introduction of the electrode tip into the internal organ of the patient; and said severing means of said introducer sleeve enabling said sleeve to be removed over the connector plug of the electrode by passing the electrode through said severing means of said sleeve.

5. An apparatus as set forth in claim 4, wherein said introducer sleeve includes a substantially tubular member having a tubular wall; and said severing means comprising a weakening in said tubular wall along the axial length thereof for enabling said introducer sleeve to be severed along said severing means.

6. An apparatus as set forth in claim 5, wherein said weakening includes perforations along said introducer sleeve.

7. An apparatus as set forth in claim 5, wherein said weakening includes a cut along the substantial length of said introducer sleeve;

and the extension of said cut terminating prior to one end of said introducer sleeve.

8. An apparatus as set forth in claim 7, wherein said introducer sleeve includes an area of reduced wall thickness in proximity to the said one end of said introducer sleeve.

9. An apparatus as set forth in claim 5 wherein said weakening includes a cut along most of the length of said introducer sleeve.

10. A method for inserting a member into an internal cavity of a patient comprising the steps of:

inserting a needle through the exterior skin of the patient and into said cavity;

introducing a guide wire through said needle and into said cavity;

withdrawing said needle;

providing a hollow, cylindrical introducer having a coaxial introducer sleeve with a preformed, longitudinal weakened line along said sleeve;

sliding said introducer and said sleeve together along said guide wire and into said cavity;

withdrawing said introducer and said guide wire from said cavity;

inserting said member through said sleeve and into said cavity; and removing said sleeve from the patient by peeling said sleeve away from said member along said weakened line.

11. A method for introducing a member into the subclavian vein of a patient, comprising the steps of:

inserting a needle through the exterior skin of the patient and into said vein;

inserting a guide wire through said needle and into said vein;

withdrawing said needle;

providing a hollow introducer having a co-axial sleeve with a longitudinal, preformed weakened line along said sleeve;

sliding said introducer and said sleeve together along said guide wire and into said vein;

withdrawing said introducer and said guide wire from said vein;

inserting said member through said sleeve and into said vein; and removing said sleeve from the patient by peeling said sleeve away from said member along said weakened line.

12. Apparatus for inserting a member into an internal cavity of a patient, comprising in combination:

a needle for puncturing the tissue of the patient to enter said cavity, said needle having an internal passage;

an introducer sleeve having a preformed, longitudinal weakened line along the length thereof;

a guide wire dimensioned to slide along the said internal passage of said needle;

an introducer fitted co-axially with said sleeve and having an internal passage dimensioned to receive said guide wire therein; and wherein said guide wire may be inserted into said cavity through said internal passage of said needle, and thereafter said introducer and said sleeve may be moved together along said guide wire into said cavity following removal of said needle therefrom, and thereafter said guide wire and said introducer may be removed from said cavity, to permit introduction of said member into said cavity through said sleeve, after which said sleeve may be removed from said member by peeling said sleeve away from said member along said weakened line.

13. The apparatus recited in claim 12 wherein said sleeve further comprises:

a tapered wall of reduced thickness in proximity to one end of said sleeve; and wherein said weakened line extends from the other end of said sleeve to the beginning of said tapered wall.

* * * * *